United States Patent [19]

Todd

[11] Patent Number: 4,568,338
[45] Date of Patent: Feb. 4, 1986

[54] PREFORMED CATHETER

[75] Inventor: Donald A. Todd, Whitehouse Station, N.J.

[73] Assignee: C. R. Bard, Inc., Murray Hill, N.J.

[21] Appl. No.: 534,774

[22] Filed: Sep. 22, 1983

[51] Int. Cl.[4] .............................. A61M 25/00
[52] U.S. Cl. .................................. 604/281
[58] Field of Search ............... 604/281, 284; 128/130

[56] References Cited

U.S. PATENT DOCUMENTS

| | | | |
|---|---|---|---|
| 3,490,446 | 1/1970 | Slonek et al. | 128/130 |
| 3,680,562 | 8/1972 | Wittes et al. | 604/281 |
| 3,920,023 | 11/1975 | Dye et al. | 604/281 |
| 3,950,360 | 9/1975 | Zaffaroni | 128/130 |
| 4,117,836 | 10/1978 | Erikson | 604/281 |
| 4,365,632 | 12/1982 | Kortum | 128/130 |
| 4,405,314 | 9/1983 | Cope | 604/281 |
| 4,495,934 | 1/1985 | Shaw, Jr. | 128/130 |

FOREIGN PATENT DOCUMENTS 0930636  7/1973  Canada .............................. 604/281

OTHER PUBLICATIONS

Bourassa, Cardiovascular Catheters, leaflet, USCI, a division of C. R. Bard, Inc., ©1972.

Primary Examiner—C. Fred Rosenbaum
Assistant Examiner—Michelle N. Lester
Attorney, Agent, or Firm—Kane, Dalsimer, Kane, Sullivan and Kurucz

[57] ABSTRACT

A catheter is disclosed which is made of a single preshaped flexible pipe. The pipe is formed into a shape resembling a figure 4. This shape prevents the catheter from being expelled from a body cavity however it is still flexible enough to be straightened by a wire pushed through the catheter for insertion.

5 Claims, 4 Drawing Figures

PREFORMED CATHETER

BACKGROUND OF INVENTION a. Field of Invention

This invention pertains to devices for introducing or removing fluids from a human body known as catheters and more particularly to a preformed catheter which has a very small diameter to be used in pediatric treatment.

b. Description of the Prior Art

Catheters for fluid injection into, or removal from a human body are well known in the art. They usually comprise a tubular body with a plurality of longitudinal bores having a distal end provided with several openings for the bore. One major problem with the catheters has been their tendency to migrate or to be expelled by the body. Various solutions have been proposed and used to solve this problem. For example some catheters have been made with sharply pointed barbs or flanges which are disposed on the outer surface of the catheter and which engage the side walls of the opening through which the catheter has been extended. However these barbs or flanges often irritate the tissues of the opening walls and may even damage them and cause serious injuries. Another approach is to provide an expandable member, such as a balloon, at the distal end of the catheter. A separate means for expanding the device must be included in the catheter, such as an inflation bore, which naturally increases its diameter. Therefore, this approach is unacceptable in certain types of operations where very thin catheters are needed, such as for example the catheters needed to drain the bladder of a four year old infant because the effective inner diameter of the bore through which drainage occurs is too small to be effective, especially if urinary salts deposit on the inner walls thereat during long term drainage. In addition the cost of making balloon-type catheters is relatively high.

OBJECTIVES AND SUMMARY OF THE INVENTION

A principal objective of this invention is to provide a catheter having a very small outer or overall diameter so that it maybe used in pediatric operations.

Another objective is to provide a catheter which is relatively simple to use.

A further objective is to provide a catheter which is easy to manufacture and inexpensive.

Other objectives and advantages shall become apparent in the following description of the invention.

The catheter of the present invention comprises a tubular body and a distal end being folded over the body across the opening through which the catheter is inserted to resist forces which tend to displace or expel the catheter. The catheter is preferably made of a flexible material of the kind which may be partially cured to preform it to a pre-selected shape and which returns to said pre-selected shape after it has been distorted.

DESCRIPTION OF THE PREFERRED EMBODIMENT

Figure 1:
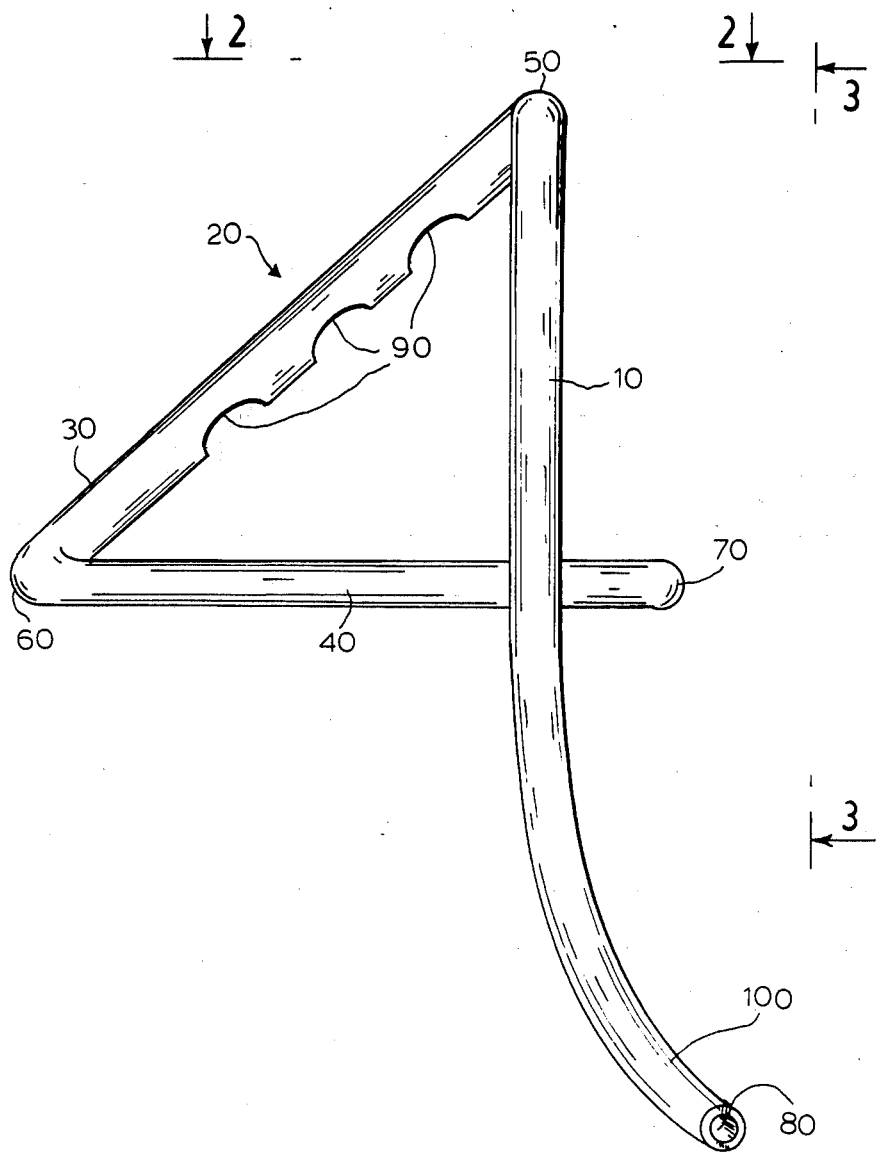
Figure 2:
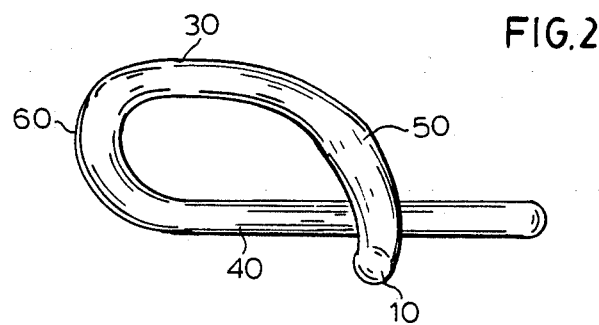
Figure 3:
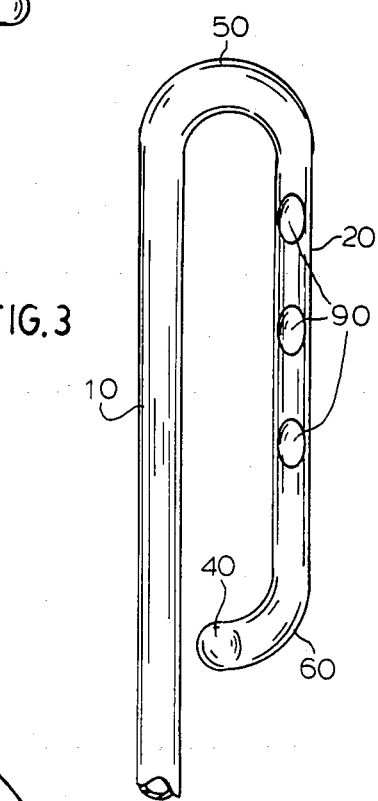
Figure 4:
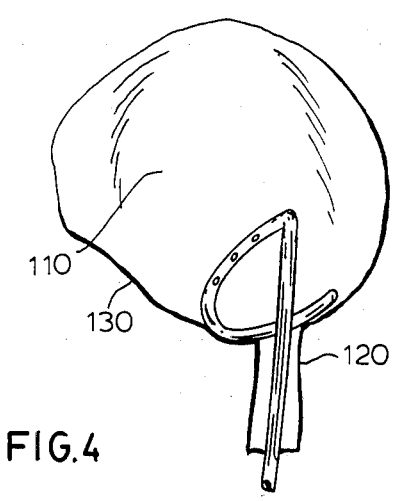

FIG. 1 shows a plan view of the catheter;
FIGS. 2 and 3 show top and side views respectively; and
FIG. 4 shows the catheter inserted in a bladder.

DESCRIPTION OF THE PREFERRED EMBODIMENT

The catheter is shown in FIGS. 1-3. It comprises a tubular body 10 and a distal end 20 attached to the tubular body in a continuous fashion. End 20 comprises a first member 30 and a second member 40. If the catheter is viewed with distal end 20 pointing forward as in FIG. 1 member 30 is oriented backward at an acute angle with body 10. A tubular curved portion 50 provides the transition between tubular body 10 and first member 30. In order to keep the overall dimensions of the distal end 20 small, curved portion 50 is oriented generally perpendicularly to the horizontal plane of FIG. 1 as shown. Similarly the transition between the first member 30 and a second member 40 is provided by a second curved portion 60. This curved portion 60 is also oriented generally perpendicularly to the plane of FIG. 1. Member 40 extends passed body 10 and ends with a closed tip 70. The portion of body 10 joined to curved portion 50 and first and second members 30 and 40 are substantially straight. Thus, as shown in FIG. 1, the distal end 20 forms with body 1 a three dimensional shape which looks like the numeral 4. In FIGS. 1-3 member 40 is shown passing behind body 10 on the same side of the body as first member 30. However the two members could also be disposed on alternate sides of body 10. For example, as seen in FIG. 1, member 30 could be behind body 10 and member 40 could be in front of said body at least while it crosses said body. Preferably as viewed from the side member 40 is closer to body 10 than member 30 and it could even touch it.

Body 10 has a generally concentric longitudinal bore 80 which is continued through curved portion 50 and substantially through member 30. Member 30 has a plurality of holes 90 communicating with bore 80. The bore 80 preferably continue through curved portion 60 and member 40 all the way to end 70 but since no further holes are provided in member 40. Depending on the intended purpose of the device holes could also be provided on member 40.

Preferably holes 90 are oriented inward to face body 10. Thus, should the catheter be used for drainage, the holes are not occluded or otherwise closed even if the distal end 20 is in contact with a tissue or cavity wall.

While the above-described components of the catheter could be made separately and then interconnected to form the desired shape, the catheter is preferably made of a single piece of tubing of the desired length which is relatively flexible but which can be preformed so that in its relaxed unstressed state it assumes the desired shape. Therefore the tubing should be made of a elastic type of material having a memory. These types of materials are well known in the art and usually comprise silicone as one of their components. The tubing may be shaped into the desired form and then partially cured, for example by applying heat to it. After cooling the tubing retains it preformed shape if allowed to relax but it is still flexible enough to be straightened. Holes 90 may be made at any time by conventional methods.

The catheter is used as follows. Prior to insertion a stiffening member such as a wire is inserted through bore 80 until the distal end 20 becomes straight and substantially colinear with body 10. In this form the catheter may be easily inserted into the body cavity. When the distal end reaches its destination, the wire is retracted and distal end 20 assumes its preformed figure 4 shape. As previously noted, the members of the distal end are flexible so that they won't injure the body cavity while they fold to their respective positions. The proximal end 100 may be connected to a preselected device for either pumping a fluid into or draining a fluid out of said cavity. In order to protect the inside surface of the bore, the wire used to straighten the catheter may be terminated by a mandrel. It should be appreciated that as the mandrel passes by holes 90 as it is inserted into or withdrawn from distal end 20 it will not pass through or engage the sidewalls of the holes because of the shape of the distal end the positioning of the holes. Instead the mandrel will tend to hug the inner wall of the bore opposite the holes.

In FIG. 4 the catheter is shown in its normal relaxed shape after it has been inserted in a body cavity 110. The inserted body 10 extends through a passage 120 communicating with the cavity. For example the cavity may be the bladder of a four year old infant. If a balloon cathether were to be used in this instance, since balloon area is two or three French sizes larger than the nominal size of the catheter shaft, an undersized catheter must be selected. Since a double lumen tube is required in such a catheter the size of the drainage lumen is so small that the drainage rate of the balloon catheter is very low and inefficient. Furthermore the catheter can be easily clogged up by solids in the fluid or capillary action.

On the other hand the single lumen construction of the present cathether provides a bore with a larger, aned more effective cross-sectional area and results in a faster, more efficient drainage rate. Furthermore, since the cross-sectional area of bore 80 is larger, there is less chance of blockage by solids or capillary action.

It should be appreciated that once the distal end achieves its preformed shape it is difficult to dislodge it from the body cavity. Any force tending to dislodge the catheter causes member 40 to come in contact with the sidewalls 130 which form the mouth of appendage 120 and prevent the catheter from being expelled from cavity 110. While the tubing forming the catheter has been preformed it is still relatively flexible. Therefore its different components act as springs. Thus when a force is applied to body 10 tending to pull distal end 20 out of the cavity, the spring action of curved portions 50 and 60 allows straight members 30 and 40 to flex toward each other absorbing the force and effectively protecting the cavity tissue from any damage.

The catheter is easily and safely removed from the body cavity simply by pulling the proximal end.

Two different sized catheters have been made in accordance with the above description of the invention for use in pediatric applications. One, a French size 6, and an outside diameter of 0.078" and a lumen of 0.044"; the other, a French size No. 8, had an outer diameter of 0.104" and a lumen of approximately 0.070".

It is clear from this description that the present invention attains all the aforementioned objectives. One skilled in the art could modify the invention without departing from its scope as defined in the appended claims.

What is claimed is:

1. A preformed catheter for insertion into a body cavity of a single piece of tubing of flexible material having a memory and at least partially cured to a relaxed unstressed state at which is assumes a pre-selected three dimensional shape and which returns to said preselected shape after it has been distorted, the catheter comprising in combination:

a tubular body having a bore;

an integral tubular distal end having a bore therethrough in communication with the bore of the body;

the distal end comprising a tubular first member and a tubular second member, a first tubular curved portion integrally connecting the first tubular member to the tubular body, a second tubular curved portion integrally connecting the first tubular member to the second tubular member, the first tubular member being disposed at an acute angle with the tubular body, the first tubular member being disposed at an acute angle with the second tubular member, the second tubular member terminating beyond the side of the tubular body opposite the side at which the second curved portion is disposed, the distal end thus defining the preselected three dimensional shape of a numeral 4, the first tubular member and second tubular member being located in respective planes both of which are on the same side of a plane in which the tubular body is located with the plane of the second tubular member being closer to the plane of the tubular body than the plane of the first tubular member, a plurality of holes in at least the first tubular member communicating with the bore and oriented inwardly towards the tubular body to prevent occlusion of the holes when the distal end is disposed in a body cavity;

whereby when a force is applied to the tubular body tending to pull the distal end out of the body cavity, the first and second curved portions permit the first and second tubular members to flex toward one another to resist this force and cooperate in preventing unintentional dislodgement of the distal end from the body cavity and at the same time protect the cavity tissue from any damage.

2. The catheter of claim 1 wherein the first tubular curved portion is substantially normal to the body and the first tubular member, the second tubular curved portion being substantially normal to the first tubular member and the second tubular member.

3. The catheter of claim 1 wherein the first and second tubular members are substantially straight.

4. The catheter of claim 1 wherein the catheter tubing is French size 6.

5. The catheter of claim 1 wherein the catheter tubing is French size 8.

* * * * *